US00PP37556P2

(12) United States Plant Patent
Korlipara

(10) Patent No.: US PP37,556 P2
(45) Date of Patent: Aug. 4, 2026

(54) ***LIATRIS* PLANT NAMED 'White Feather'**

(50) Latin Name: *Liatris spicata*
Varietal Denomination: White Feather

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 19/429,837

(22) Filed: Dec. 22, 2025

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Klarquist Sparkman, LLP

(57) ABSTRACT

A new and distinct *Liatris* cultivar named 'White Feather' distinguished by a compact branching habit, high number of bright white inflorescences, and first year blooming.

2 Drawing Sheets

Latin name of the genus and species of the plant claimed: *Liatris spicata.*

Variety designation: 'White Feather'.

BACKGROUND

The present application relates to a new and distinct cultivar of *Liatris* named 'White Feather'. *Liatris* is in the family Asteraceae. The new cultivar 'White Feather' originated as a planned breeding program to produce varieties that flower in year one.

SUMMARY

The new plant resulted from a cross of seed donor (female) parent '*Liatris* 14-22' (unpatented) and an unknown pollen donor (open pollination). '*Liatris* 14-22' is proprietary breeding stock and is not publicly available. The new cultivar, 'White Feather', was selected when growing in a cultivated area in Canby, Oregon.

The new *Liatris* cultivar 'White Feather' is distinguished from other *Liatris* varieties due to the following unique combination of characteristics:

1. First year flowering
2. Compact habit
3. Excellent branching
4. High number of bright white inflorescences The new variety is distinct from other known *Liatris* varieties. A comparison to several varieties is provided in Table 1 below.

TABLE 1

Comparison of 'White Feather' to known *Liatris* varieties.

| Comparison Variety | Trait | Expression of Trait in Comparison Variety | Expression of Trait in 'White Feather' |
|---|---|---|---|
| *Liatris spicata* 'Alba' (unpatented) | Height | 90 cm | 70 cm |

TABLE 1-continued

Comparison of 'White Feather' to known *Liatris* varieties.

| Comparison Variety | Trait | Expression of Trait in Comparison Variety | Expression of Trait in 'White Feather' |
|---|---|---|---|
| *Liatris spicata* 'Alba' (unpatented) | Width | 30-60 cm | 65 cm |
| *Liatris spicata* 'Floristan White' (unpatented) | Height | 90 cm | 70 cm |
| *Liatris spicata* 'Floristan White' (unpatented) | Width | 23 cm | 65 cm |

As shown in Table 1, the claimed variety is shorter and wider than both *Liatris spicata* 'Alba' (unpatented) and *Liatris spicata* 'Floristan White' (unpatented).

The new cultivar has been reproduced by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oregon, shows that the characteristics described herein come true to form, are firmly fixed, and are established and transmitted through succeeding propagations.

Figure 1:
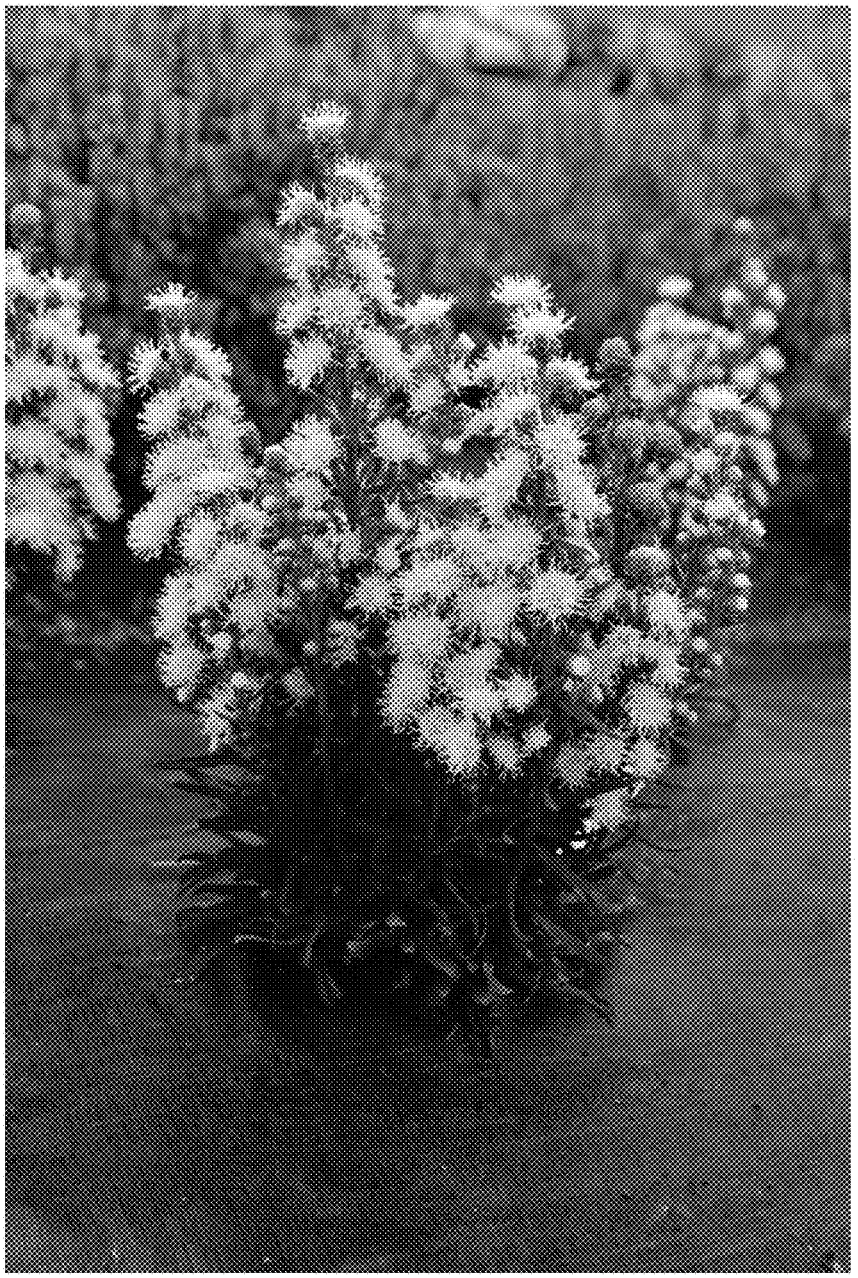
FIG. 1 shows a 9-month-old plant, field grown in full sun in Canby, Oregon. The photograph was taken in September 2024.
Figure 2:
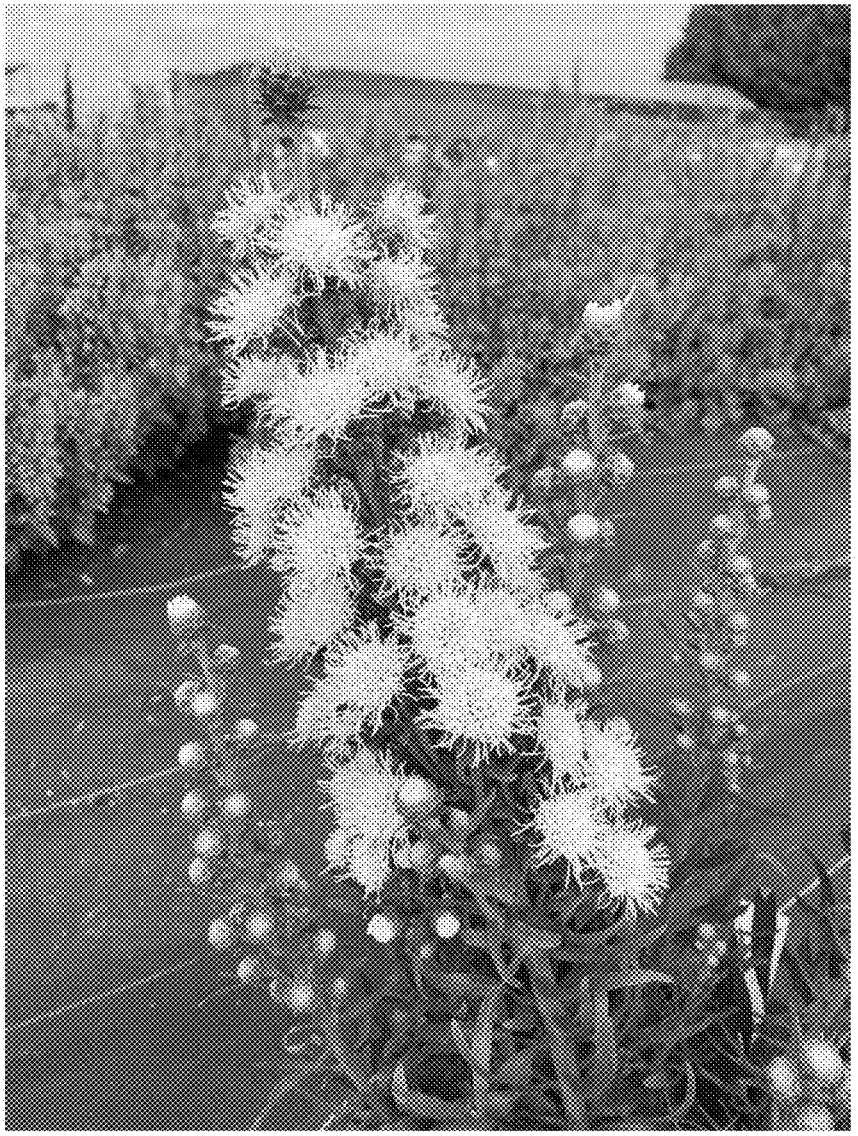
FIG. 2 shows an inflorescence on a 9-month-old plant that was field grown in full sun in Canby, Oregon. The photograph was taken in September 2024.

The color photographs show typical specimens of the new cultivar and depict the color as nearly true as is reasonably possible. It should be noted that colors may vary, for example due to lighting conditions at the time the photograph is taken. Therefore, color characteristics of this new cultivar should be determined with reference to the observations described herein, rather than from the photograph alone.

DETAILED PLANT DESCRIPTION

The following is a detailed description of the new *Liatris* cultivar based on observations taken in the month of September of a 20-month-old asexually reproduced progeny grown in full sun exposure in a field in Canby, Oregon. Canby is Zone 8 on the USDA Hardiness map. Temperatures range from a high of 95° F. in August to an average of 32° F. in January. Normal rainfall in Canby is 42.8 inches per year.

The new cultivar has not been evaluated under all possible environmental conditions and certain characteristics may change with changing environmental conditions (such as photoperiod, temperature, moisture, soil conditions, nutrient availability, or other factors). The phenotype may change with variations in environment without a change in the genotype of the plant.

Color descriptions and other terminology are used in accordance with their ordinary dictionary descriptions, unless the context clearly indicates otherwise. Color descriptions used herein are made with reference to *The Royal Horticultural Society Colour Chart,* $5^{th}$ edition, 2007

Parentage:

*Female parent.*—'*Liatris* 14-22'.

*Male parent.*—Unknown, Open Pollinated.

Plant:

*Type.*—Herbaceous perennial.

*Hardiness.*—USDA zones 4-9.

Size:

*Width.*—65 cm at widest point.

*Height.*—70 cm to top of inflorescence.

*Form/growth habit.*—Basal clump.

*Number of crowns.*—3-7.

*Vigor.*—Good.

Roots:

*Description.*—Fibrous.

*Color.*—Closest to RHS NN155B.

*Color of corms.*—Closest to RHS N199B.

Stem (flowering):

*Type.*—Ascending with up to approximately 200-300 inflorescences per stem.

*Size.*—Up to 70 cm tall at terminal inflorescence and up to 17 mm wide at base.

*Strength.*—Strong.

*Internode length.*—1-3 cm.

*Surface texture.*—Puberulent.

*Rugosity.*—Minor to none.

*Variegation.*—None.

*Color.*—RHS 143A.

*Base becoming lignified.*—RHS 199A.

Leaves:

*Type.*—Simple.

*Shape.*—Linear.

*Arrangement.*—Alternate.

*Blade size.*—Length: Up to 12 cm. Width: Up to 1.75 cm at widest point.

*Margins.*—Entire, ciliate.

*Apex.*—Acute.

*Base.*—Attenuate.

*Surface texture.*—Foveolate.

*Venation.*—Pinnate.

*Vein color.*—RHS 144D.

*Leaf color.*—Upper Surface: RHS 147A. Lower Surface: RHS 147B.

*Petiole description.*—Sessile.

Inflorescence:

*Type.*—Terminal raceme.

*Flowering stem.*—Description: Unbranched to branched with 100-200 inflorescences per central stem, 1-40 inflorescences per secondary branched stem. Height: Up to approximately 70 cm.

*Form.*—Upright.

*Immature inflorescence* (*bud*).—Width: 1.0 cm. Height: 1.2 cm. Color: RHS 143C.

*Mature inflorescence.*—Size: Up to 3 cm wide and 3 cm deep. Pedicel: 1-2 cm, Color RHS 144B.

*Florets.*—Number: Approximately 35. Length: 1.5-2.0 cm overall. Width: 6 mm at widest point. Number of lobes of corollas: 5. Corolla length: 8 mm. Corolla width: 2 mm at widest part of tube with 9 mm spread at apex; 5 mm long feather like barbellate structures fused at base of corolla tube, 20-30 in number. Base tubular or not: Tubular. Lobes spreading or not: Spreading. Texture outside: Corolla cancellate. Inside texture: Hirsuit at base.

*Inside and outside corolla tube color.*—Tip: RHS NN155D. Base: RHS160D. Center of Corolla: Entirely semi translucent.

*Pistil.*—Description: 1 pistil present, 5 stamens fused in the center with 2 sigma branches protruding above, nectaries are present at base of pistils. Pistil length: 17 mm. Pistil width: 1 mm. Pistil color: RHS NN155A, RHS 158A at tip. Ovary subtending: Covered in medium-long fine white hairs. Ovary size: 1.5 mm wide, 5 mm long. Ovary color: Between RHS 145C and 145D. Ovule length: 3-4 mm long, 1 mm wide. Ovule color: translucent RHS 155D. Style length: 15 mm. Style color: RHS NN155C touched with RHS N155B at base of branching. Style branched or not: Branched. Stigma Description: Undistinguished from style branches. Style branching spread: 4-15 mm, becoming more spread as floret matures.

*Stamen.*—Stamen length: 10-11 mm. Anther length: 5-6 mm. Anther color: Begins as RHS 158A with tips touched with RHS 182D, maturing closest to RHS 168D. Anthers fused surrounding pistil. Filament length: 5 mm. Filament color: RHS NN155D. Filaments have short white hairs at base.

*Pollen present or not.*—Present.

*Pollen color.*—Closest to RHS NN155D.

*Involucral bracts.*—Size: In 6-8 leafy series, up to 12 mm wide and 18 mm deep. Lobe shape: Oblong to obdeltoid. Lobes reflexed or not: Slightly reflexed at base. Lobe length: Up to 9 mm. Lode width: Up to 5 mm at widest point. Lobe color: Outside tip closest to RHS 137A, outside base closest to RHS 145A, inside tip closest to RHS 144A, and base closest to RHS 145C. Lobe margins: Margins translucent and slightly irregularly serrate. Lobe tip: Emarginate. Lobe base: Rounded. Lobe surface texture: Pubulerent.

*Receptacle*.—Size: Grows up to 6 mm wide and 5 mm deep. Color: Closest to RHS 13D, oxidizes quickly.

*Bloom period*.—August-October in Canby, Oregon.

*Fragrance*.—Mild, pleasant.

*Lastingness*.—Each flowering stem lasts for 3-4 weeks in Canby, Oregon.

Seed: None seen at time of observation.

Disease and pests: Susceptible to thrips.

I claim:

1. A new and distinct *Liatris* plant named 'White Feather' substantially as illustrated and described herein.

* * * * *